United States Patent
Dingerdissen et al.

(10) Patent No.: US 8,378,127 B2
(45) Date of Patent: Feb. 19, 2013

(54) METHOD FOR PRODUCING 2,6-DIOXABICYCLO-(3.3.0)-OCTANE-4,8-DIONE

(75) Inventors: Uwe Dingerdissen, Seeheim (DE); Jan Pfeffer, Essen (DE); Thomas Tacke, Alzenau (DE); Thomas Haas, Muenster (DE); Harald Schmidt, Muelheim an der Ruhr (DE); Michael Volland, Duelmen (DE); Michael Rimbach, Herne (DE); Christian Lettmann, Coesfeld (DE); Roger Sheldon, Hoog-Kappel (NL); Michiel Janssen, The Hague (NL)

(73) Assignee: Evonik Degussa GmbH, Essen (DE)

( * ) Notice: Subject to any disclaimer, the term of this patent is extended or adjusted under 35 U.S.C. 154(b) by 50 days.

(21) Appl. No.: 13/142,883

(22) PCT Filed: Jan. 26, 2010

(86) PCT No.: PCT/EP2010/050832
§ 371 (c)(1),
(2), (4) Date: Jun. 30, 2011

(87) PCT Pub. No.: WO2010/089223
PCT Pub. Date: Aug. 12, 2010

(65) Prior Publication Data
US 2011/0269977 A1    Nov. 3, 2011

(30) Foreign Application Priority Data

Feb. 6, 2009 (DE) .......................... 10 2009 000 661
Jun. 3, 2009 (DE) .......................... 10 2009 026 673

(51) Int. Cl.
*C07D 493/02* (2006.01)

(52) U.S. Cl. .......................... 549/464; 549/429; 549/456
(58) Field of Classification Search .................. 549/429, 549/456, 464
See application file for complete search history.

(56) References Cited

U.S. PATENT DOCUMENTS

| 4,543,168 | A | 9/1985 | Fleche et al. |
| 5,136,103 | A | 8/1992 | Fried |
| 6,884,887 | B1 | 4/2005 | Riermeier et al. |
| 7,030,279 | B1 | 4/2006 | Tanielyan et al. |
| 7,145,041 | B2 | 12/2006 | Kuehnle et al. |
| 7,230,134 | B2 | 6/2007 | Borner et al. |
| 2010/0094058 | A1 | 4/2010 | Lettmann et al. |
| 2010/0324257 | A1 | 12/2010 | Karau et al. |

FOREIGN PATENT DOCUMENTS

WO    2010 127970    11/2010

OTHER PUBLICATIONS

Heyns, K. et al., "Selektive Katalytische Oxydation Von 1.4;3.6-Dianhydro-hexiten", Chemische Berichte, Uber Katalytische Oxydation (XX), vol. 96, No. 12, pp. 3195-3199, XP-002579295, (1963).
International Search Report Issued May 18, 2010 in PCT/EP10/050832 filed Jan. 26, 2010.
U.S. Appl. No. 13/140,921, filed Jun. 20, 2011, Dingerdissen, et al.
U.S. Appl. No. 13/263,761, filed Oct. 10, 2011, Haas, et al.
U.S. Appl. No. 13/143,354, filed Jul. 6, 2011, Sieber, et al.

*Primary Examiner* — Golam M M Shameem
(74) *Attorney, Agent, or Firm* — Oblon, Spivak, McClelland, Maier & Neustadt, L.L.P.

(57) ABSTRACT

The invention relates to a method for producing 2,6-dioxabicyclo-(3.3.0)-octane-4,8-dione (I), comprising the oxidation of dianhydrohexitols (II-IV), or of corresponding hydroxy ketones, with an oxygen-containing gas in the presence of a catalyst composition, the reaction proceeding without the addition of halogen sources.

15 Claims, 4 Drawing Sheets

Fig. 1: Oxidation of isosorbitol with AA-Tempo/nitrite/nitrate/oxygen

Fig. 2: Oxidation of isosorbitol with AA-Tempo/nitrate/ oxygen

Fig. 3: Oxidation of isomannitol with AA-Tempo/nitrate/ oxygen

Fig. 4:

METHOD FOR PRODUCING 2,6-DIOXABICYCLO-(3.3.0)-OCTANE-4,8-DIONE

The present invention relates to a process for preparing (2,6-dioxabicyclo[3.3.0]octane-4,8-dione)(I)

from favorably accessible anhydro sugars, also called dianhydrohexitols, such as 1,4:3,6-dianhydro-D-mannitol (II), 1,4:-3,6-dianhydro-D-glucitol (isosorbitol), (III) and 1,4:3,6-dianhydro-L-iditol (IV).

(2,6-Dioxabicyclo[3.3.0]octane-4,8-dione) (I), also called D-threo-2,5-hexodiulose or 1,4:3,6-dianhydro-(7CI, 8CI, 9CI)-(furo[3,2-b]furan), is an important synthesis building block and can be obtained from natural sources.

The oxidation of sugar building blocks, such as L-sorbose, D-glucitol and D-fructose, to 2,6-dioxabicyclo[3.3.0]octane-4,8-dione is described in, for example, G. C. Whiting and R. A. Coggins (Chemistry & Industry, 1963 (49), 1925-1926) as a stoichiometric conversion with bromine as oxidizing agent. Also accomplished is the conversion of (poly)saccharides with an excess of sodium nitrite as oxidant to the corresponding oxidized compounds (T. J. Painter et al., Carbohydrate Res. 55, 95-103 (1977), ibid. 140, 61-68 (1985).

In addition to the stoichiometric conversions, catalytic conversions have also been described.

The oxidation of the endo-positioned hydroxyl groups of 1,4:3,6-dianhydrohexitol in the presence of colloidal platinum as catalyst is described by Heynes et al. in *Chemische Berichte* (1963) 96(12), 3195-3199, and also in German Laid-Open Specification DE 14 43 385. The oxidation of 1,4:3,6-dianhydro-D-mannitol (II) yields the diketone (I). In contrast, in the oxidation of 1,4:3,6-dianhydro-D-glucitol (isosorbitol)c (III), only one of the hydroxyl groups is oxidized, and so a hydroxyketone is formed (4-hydroxy-2,6-dioxabicyclo-[3.3.0]octan-8-one [1S,4S,5R])(V):

The oxidation of 1,4:3,6-dianhydro-L-iditol (IV) by means of this process, however, is unsuccessful. Neither of the OH groups can be oxidized. Logically, Heynes opines that the reaction of strongly hindered, i.e., exo-positioned, OH groups by this method is not successful.

Another method for this oxidation is described by Jacquet et al. in *Journal of Chemical Technology and Biotechnology* (1990) 48(4), 493-506. Here again, the only conversion successfully achieved is of the 1,4:3,6-dianhydro-D-glucitol (isosorbitol) (III) to the hydroxyketone (4-hydroxy-2,6-dioxabicyclo[3.3.0]octan-8-one [1S,4S,5R]) (V).

The electrochemical oxidation of 1,4:3,6-dianhydro-D-mannitol (II) and 1,4:3,6-dianhydro-D-glucitol (isosorbitol) (III) with sodium bromide as electrolyte is described by US patent specification U.S. Pat. No. 4,543,168. There as well, 1,4:3,6-dianhydro-D-mannitol (II) was oxidized partly to the diketone (I), whereas for 1,4:3,6-dianhydro-D-glucitol (isosorbitol) (III) only the endo-positioned hydroxyl group could be oxidized to form the hydroxyketone (V).

U.S. Pat. No. 7,030,279 describes, generally, the oxidation of primary or secondary alcohols with oxygen as oxidant to form the corresponding aldehydes and ketones by means of a catalyst system composed of a free nitroxyl radical derivative, a nitrate source, a bromine source, and a carboxylic acid, the carboxylic acid in all cases being acetic acid.

Xinquan Hu et al. in J. AM. CHEM. SOC. 2004, 126, 4112-4113 describe the oxidation of alcohol by means of nitroxyl radical derivative and oxygen, the nitrate source being replaced by a nitrite source. In this case, however, it is stated explicitly that there is no way of avoiding the use of a bromine source. The solvent listed in the examples described is dichloro-methane.

The processes of the prior art have the disadvantage that, owing to the low yields and numerous process steps or to the stoichiometric use of expensive and toxic reagents, they are unsuitable for industrial preparation of 2,6-dioxabicyclo [3.3.0]octane-4,8-dione. In particular, the additions of bromine sources in conjunction with carboxylic acids or in organic solvents, which are required in the case of the nitroxyl radical-catalyzed conversion of alcohols, constitute extremely corrosive systems which are an impediment to a transfer to the industrial scale.

The object of the present invention, therefore, was that of providing a process for preparing 2,6-dioxa-bicyclo[3.3.0]octane-4,8-dione (I) that avoids the abovementioned disadvantages and can be implemented in an economically advantageous way.

Surprisingly, a process has been found for preparing 2,6-dioxabicyclo[3.3.0]octane-4,8-dione (I) using as starting material the respective anhydro-sugar 1,4:3,6-dianhydro-D-mannitol (II), 1,4:3,6-dianhydro-D-glucitol (isosorbitol), (III) or 1,4:3,6-dianhydro-L-iditol (IV). In addition, however, the corresponding hydroxyketones can, particularly the hydroxyketone (V), can be used in the process of the invention.

The invention accordingly provides a process for preparing 2,6-dioxabicyclo[3.3.0]octane-4,8-dione (I) comprising the oxidation of dianhydrohexitols (II-IV), or of corresponding hydroxyketones, more particularly of hydroxyketone (V) to give the hexodiulose (I), with an oxygen-containing gas in the presence of a catalyst composition comprising at least one nitroxyl radical, one or more NO sources, such as nitrate, nitrite or a nitrogen oxide gas, for example, and at least one or more carboxylic acids or their anhydrides and/or mineral acids or their anhydrides, optionally in the presence of one or more solvents, the reaction taking place without addition of halogen sources.

The process of the invention has the advantage that the anhydro-sugar is oxidized by a mild method in the presence of nitroxyl radicals in a single process step. Using this mild method it is possible, surprisingly, to oxidize not only the endo-position but also the exo-position secondary hydroxyl groups of the bicyclically cis-linked, five-membered ring systems to keto groups. In this conversion, particularly when using 1,4:3,6-dianhydro-D-glucitol (III) as starting material, a quantitative conversion can be achieved, with the diketone (I) being formed with a selectivity of up to 100%, optionally alongside relatively small amounts of the hydroxyketone (V). Similar conversions are also successfully accomplished with 1,4:3,6-dianhydro-D-mannitol (II) and possibly also with 1,4:3,6-dianhydro-L-iditol (IV). Success is achieved more particularly in avoiding corrosive halogen sources and in tailoring the substrate that constitutes the NO source to the particular operational requirements, by variation, in such a way as to ensure simple work-up of the reaction discharge. A particular advantage, however, is that the process is accomplished without addition of external halogen sources, in other words in a halogen-free operation. Halogen sources for the purposes of the present invention are all halogen-containing compounds which are able to release halogens in elemental form or halogen-containing ions in any oxidation state. The addition of halogen-containing compounds, such as chlorites or bromine-containing compound such as N-bromosuccinimide, N-bromophthalimide, tetrabutyl-ammonium bromide or inorganic salts, such as $NH_4Br$, alkali metal bromides or alkaline earth metal bromides, for example, for implementing the oxidation, is therefore unnecessary, in contrast to the prior art. The result is that the process product obtained as well is very largely halogen-free, with halogen-free for the purposes of the present invention meaning that no halogen originates from an external halogen source. In the process of the invention it is preferred to use dianhydrohexitols selected from 1,4:3,6-dianhydro-D-mannitol (II), 1,4:3,6-dianhydro-D-glucitol (isosorbitol (III), and 1,4:3,6-dianhydro-L-iditol (IV). 1,4:3,6-Dianhydro-D-glucitol (isosorbitol) (III) is used with particular preference as starting material.

The oxidation in the process of the invention is carried out with a catalyst composition in the absence of transition metals.

Key constituent of the catalyst composition used in the process of the invention are the nitroxyl radicals. In the context of this invention, nitroxyl radicals are compounds which comprise the atomic moiety and which are stable at room temperature for at least one week in the presence of oxygen. These nitroxyl radicals have no hydrogen atoms on the α-C atom adjacent to the nitrogen atom.

In the process of the invention it is preferred, as nitroxyl radicals in the catalyst composition, to use compounds in accordance with the structure (VI) and/or saltlike compounds in accordance with the structure (VII):

(VI)

(VII)

where:
$R^1, R^2, R^3, R^4, R^5$ and $R^6 = (C_1-C_{10})$-alkyl, $(C_1-C_{10})$-alkenyl, $(C_1-C_{10})$-alkoxy, $(C_6-C_{18})$-aryl, $(C_7-C_{19})$-aralkyl-, $(C_6-C_{18})$-aryl-$(C_1-C_8)$-alkyl or $(C_3-C_{18})$-heteroaryl group,
the substituents of the type $R^1$, $R^2$, $R^3$, $R^4$, $R^5$ and $R^6$ being identical or different and the substituents of the type $R^5$ and $R^6$ being able together to form a $(C_1-C_4)$alkylene bridge, which may be saturated or unsaturated, unsubstituted or substituted, more particularly by one or more substituents selected from $R^1$, $C_1-C_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino group.

In the structure (VII) $Y^-$ is any desired halogen-free anion.

In the process of the invention it is possible to use either a nitroxyl radical or else a mixture of different nitroxyl radicals.

As nitroxyl radicals in the process of the invention it is preferred to use 2,2,6,6-tetramethylpiperidine-1-oxyl (TEMPO) and/or the derivatives of 2,2,6,6-tetramethylpiperidine-1-oxyl which are substituted in position 4 of the heterocycle, the derivatives having one or more substituents selected from $R^1$, $C_1-C_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups, where $R^1$ is a $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl or $(C_3-C_{18})$-heteroaryl group. Examples of corresponding compounds are 4-methoxy-2,2,6,6-tetramethylpiperidine-1-oxyl (4-MeO-TEMPO), 4-oxo-2,2,6,6-tetramethylpiperidine-1-oxyl (4-oxo-TEMPO), 4-hydroxy-2,2,6,6-tetramethylpiperidine-1-oxyl (4-hydroxy-TEMPO), 4-benzoyloxy-2,2,6,6-tetramethylpiperidine-1-oxyl (BnO-TEMPO), 4-acetamido-2,2,6,6-tetramethylpiperidine-1-oxyl, 4-acetamino-2,2,6,6-tetramethylpiperidine-1-oxyl (AA-TEMPO), 4-amino-2,2,6,6-tetramethylpiperidine-1-oxyl, N,N-di-methylamino-2,2,6,6-tetramethylpiperidine-1-oxyl (NNDMA-TEMPO), 3,6-dihydro-2,2,6,6-tetramethyl-1(2H)-pyridinyloxyl (DH-TEMPO) or bis(2,2,6,6-tetramethyl-piperidine-1-oxyl-4-yl) sebacate, it being possible for the stated examples to have one or more substituents selected from $R^1$, $C_1$-$C_8$-amido, halogen, oxy, hydroxyl, amino, alkylamino, dialkylamino, arylamino, diaryl-amino, alkylcarbonyloxy, arylcarbonyloxy, alkylcarbonylamino and arylcarbonylamino group.

The tetramethylpiperidine-N-oxyl structural fragment in accordance with the structures (VI) or (VII) may also be part of a larger macromolecule, of an oligomer or else of a polymer structure. One example of such a nitroxyl radical is shown by the structure (VIII):

(VIII)

The nitroxyl radicals may also be used in heterogeneous form in the process of the invention, which means that the nitroxyl radicals are applied on a support, such as aluminum oxide, silicon dioxide, titanium dioxide or zirconium dioxide, for example. As support material for the nitroxyl radical it is also possible to use polymers, composites or carbon. In another embodiment the nitroxyl radicals may also be present in immobilized form, such as in gel particles, capsules or polymer matrices, for example.

In the process of the invention it is preferred to use the abovementioned compounds AA-TEMPO, 4-hydroxy-TEMPO, TEMPO and 4-oxo-TEMPO as nitroxyl radicals. Particular preference is given to using AA-TEMPO, 4-hydroxy-TEMPO and TEMPO, and especially AA-TEMPO.

In the process of the invention the fraction of nitroxyl radical is preferably 0.001 to 10 mol %, more preferably 0.01 to 5 mol % and very preferably 0.1 to 2 mol %, based on the amount of dianhydrohexitol used.

The catalyst composition used in the process of the invention further comprises at least one NO source. As NO source in the process of the invention it is possible to use, for example, nitric acid, nitrous acid, ammonium nitrate or ammonium nitrite, or alkali metal or alkaline earth metal nitrates or nitrites, such as magnesium nitrate, for example, or sodium nitrite. Furthermore, in addition to or as a substitute for the nitrates or nitrites, it is possible to use nitrogen oxide-containing gases such as $N_2O$, NO, $N_2O_3$, $NO_2$, $N_2O_4$ and $N_2O_5$. As NO source it is also possible to use mixtures of different NO sources among those identified above. In the process of the invention the fraction of NO source(s) used is 0.001 to 10 mol %, preferably from 0.01 to 5 mol % and very preferably from 0.1 to 2 mol %, based on the amount of dianhydrohexitol used.

The catalyst composition used in the process of the invention further comprises at least one or more carboxylic acids or their anhydrides and/or mineral acids or their anhydrides. As carboxylic acid or carboxylic anhydride in the process of the invention it is preferred to use acetic acid or acetic anhydride, propionic acid or another carboxylic acid or another anhydride which dissolves in the reaction mixture. In the process of the invention it is preferred to use acetic acid. It is also possible to use mixtures of different suitable carboxylic acids or solutions of carboxylic acids in a suitable solvent. The fraction of at the at least one carboxylic acid is preferably 0.1 to 200 mol %, more preferably 10 to 50 mol %, based on the amount of dianhydrohexitol used.

For the purposes of the present invention the term "mineral acids" is used as a collective designation for all inorganic acids. Suitable mineral acids are, for example, $H_2CO_3$, $H_3PO_4$, $HNO_3$, $HNO_2$, $H_2SO_4$, $H_2SO_3$, $H_3BO_3$ or their anhydrides or mixtures thereof.

As oxidizing agent in the process of the invention an oxygen-containing gas is used. As oxygen-containing gas it is possible to use pure oxygen, although mixtures of oxygen with an inert gas or air or with a gas which participates in the reaction may also be used. Examples of suitable inert gases include nitrogen, carbon dioxide, helium and argon. Gases that participate in the reaction and may be used include, for example, nitrogen oxides, which have already been specified above in the description of the NO sources. The partial pressure of the oxygen is preferably 0.1 to 100 bar, more preferably 0.2 to 50 bar.

The process of the invention can be carried out in a solvent or without use of a solvent:

In one particular embodiment of the process of the invention, the process step is carried out in the presence of a solvent. In this case it is preferred to use polar solvents, more particularly polar organic solvents. As solvents it is preferred to use acetonitrile, tetrahydrofuran, ethyl acetate, acetone, diethyl ether, methyl tert-butyl ether, tertiary alcohols such as tert-amyl alcohol, tert-butyl alcohol, esters of carbonic acid such as dimethyl carbonate, diethyl carbonate, hydrocarbons, or a mixture of these solvents. It is preferred to use 0.1% to 70% by volume, preferably 0.5% to 60% by volume and very preferably 1% to 50% by volume of solvent, based on the amount of dianhydrohexitol used.

In another preferred embodiment of the process of the invention no additional solvent is used. In this case the carboxylic acid or the mineral acid serves not only as a component of the catalyst composition but also as a solvent, in order to keep the reaction mixture homogeneous. This has the advantage that it is possible to do without flammable and possibly health-injurious solvents, and that separate removal of the solvent is unnecessary.

Elucidated below is the implementation of the process of the invention. The oxidation in the process of the invention is carried out preferably at a temperature of 0 to 100° C. or at the boiling point of the solvent.

The total pressure during the oxidation in the process of the invention is preferably 1 to 300 bar, more preferably 1 to 50 bar.

The process can be carried out as a batch, semibatch or continuous process. Moreover, the process of the invention is not tied to any particular type of reactor, and instead the process step can be carried out in a stirred tank, in a tube reactor, in a tank cascade, in a microreactor or in a combination of these reactor types. The catalyst in this case may be present homogeneously or in heterogeneous form as described above.

In one embodiment of the process of the invention the dianhydrohexitol is first dissolved or suspended in a suitable solvent and then the catalyst composition is added to this solution or suspension, individually or as a mixture.

Pressure and temperature are then set. It is also possible, however, to introduce the catalyst composition to start with and to add the solution or suspension of the dianhydrohexitol to the catalyst composition. In the case of a continuous process regime, the alcohol is preferably supplied with the reaction gases in a fluidized bed embodiment.

In one preferred embodiment of the process of the invention the reaction can be accelerated by removing the water of reaction from the reaction mixture. For this purpose the reaction mixture is admixed with water-absorbing agents, preferably sodium sulfate, calcium oxide and molecular sieves, e.g., zeolites. For example, the abovementioned mineral acids and/or their anhydrides may be used as water-binding acids. An additional possibility is to use solvents which effect very great complexing of water, such as glacial acetic acid, for example. It is also possible, furthermore, to use solvents which are able to bind water chemically. These are preferably the anhydrides of the carboxylic acids used in the process of the invention. Hence the carboxylic anhydrides act not only as solvents for the reaction but also simultaneously as water-binding agents. In this way, an efficient reaction regime is enabled, which at the same time leads to high yields—an effect unknown in this way from the prior art.

The water of reaction can be stripped from the reaction mixture either by distillative removal or by extractive removal from the reaction events.

The reaction mixture is generally worked up in dependence on the polarity of the target molecules and the solubility of the nitroxyl radicals. In the case of 2,6-dioxabicyclo[3.3.0]octane-4,8-dione, which has very good water-solubility and is present in its dihydrate form in water, the following procedure is appropriate:
a) removal of the solvents and the carboxylic acid by distillation or extraction
b) extraction and optionally recycling of the nitroxyl radicals
c) removal of any salts originating from the NO sources by ion exchangers, electrodialysis, reverse osmosis, membrane techniques or ultrafiltration
d) and/or purification of the product by crystallization, distillation, extraction and/or chromatographic separation.

The stated process steps may be carried out alone or in any desired combination with one another.

The 2,6-dioxabicyclo[3.3.0]octane-4,8-dione (I) obtained in accordance with the process of the invention can be used advantageously as an intermediate for further reaction. For example, the diketone may be converted by reductive amination with ammonia, hydroxylamine or hydrazine into the corresponding amines or diamines, which can be used advantageously as raw material for the production of plastics. Alternatively the resulting 2,6-dioxabicyclo[3.3.0]-octane-4,8-dione (I) may be subjected to hydrocyanation—in other words, hydrogen cyanide can be added onto the keto groups under acid catalysis. The addition products obtained may be converted into α-hydroxy-carboxylic acids, α-aminocarboxylic acids (amino acids), unsaturated carboxylic acids or amines. Processes of this kind are known to the skilled person and can be carried out in a simple way.

For example, the reductive amination can be carried out in one stage or else in two or more stages. It is preferred to carry out the reductive amination in one stage. In that case the 2,6-dioxabicyclo[3.3.0]octane-4,8-dione (I) is subjected to aminating hydrogenation directly in the presence of ammonia, hydrogen, a hydrogenation catalyst and, optionally, further additions, such as molecular sieve, for example, and in the presence or absence of organic solvents.

In the case of a multistage process the hexodiulose is first converted into the corresponding diimine in the presence of ammonia (process step a)) and then hydrogenated (process step b)). The diimine used in process step b) may be used either as pure substance or else as a direct process product from process step a).

In order to accelerate the establishment of equilibrium in the imination in process step a) it is useful to use what is called an imination catalyst. For this purpose, in process step a) of the process of the invention, it is possible to use the imination catalysts known in accordance with the prior art. Preference is given to using imination catalysts selected from inorganic or organic ion exchangers, supported heteropolyacids, acidic metal oxides, more particularly aluminum oxide and titanium dioxide, organopolysiloxanes containing sulfonic acid groups, and acidic zeolites. Activated carbons treated with mineral acids may also be employed. The imination catalyst used in process step a) may be present in the form of a suspended catalyst or fixed-bed catalyst.

The imination catalyst and the hydrogenation catalyst are preferably each arranged in a separate reactor. It is also possible, though, to arrange the imination catalyst together with the hydrogenation catalyst in the same reactor. It is also possible to employ what are called bifunctional catalysts, which catalyze both the imination and the hydrogenation. Examples of catalysts of this kind are hydrogenation catalysts applied on inorganic or organic support materials from the groups specified above.

The imination in process step a) of the process of the invention is carried out preferably at a reaction temperature of 10 to 150° C., more preferably of 30 to 130° C. and very preferably of 40 to 100° C.

The pressure in process step a) of the process of the invention is preferably from the autogenous pressure of the reaction mixture to 50 MPa, more preferably from 0.3 to 50 MPa and very preferably from 5 to 30 MPa. With very particular preference, process step a) is carried out at the same pressure as process step b)—the hydrogenation.

In one preferred embodiment of the process of the invention the equilibrium of the imination in process step a) is shifted in the direction of the diimine, by removing the water formed during the imination. For this purpose, in process step a), water-absorbing agents are added to the reaction mixture, preferably molecular sieves, calcium oxide and sodium sulfate. Particularly suitable for this purpose are molecular sieves, preferably molecular sieves having a pore size of 4 angströms.

For each mole of 2,6-dioxabicyclo[3.3.0]octane-4,8-dione (I) used in process step a) of the process of the invention it is preferred to use from 1 to 500 mol, more preferably from 5 to 200 mol, of ammonia.

The imination of hexodiulose in process step a) of the process of the invention takes place preferably with liquid ammonia. More preferably this imination is carried out without the addition of further solvents. It is possible, though, to carry out process step a) in the presence of additional solvents as well. Suitable solvents for this purpose are monohydric alcohols having 1 to 4 carbon atoms, more particularly methanol, and also ethers, more particularly tetrahydrofuran, methyl tert-butyl ether or dioxane. The use of mixtures of the abovementioned solvents is possible as well.

As hydrogenation catalysts it is possible in process step b) of the process of the invention to use in principle all catalysts which are capable of catalyzing the hydrogenation of nitrile groups and/or imine groups with hydrogen. Particularly suitable for this purpose are nickel, copper, iron, palladium, rhodium, ruthenium, and cobalt catalysts; cobalt catalysts are especially suitable. In order to increase the activity, selectivity and/or service life, these hydrogenation catalysts may further comprise doping metals or other modifiers. Typical doping metals are, for example, Mo, Fe, Ag, Cr, Ni, V, Ga, In, Bi, Ti, Zr and Mn, and also the rare earths. Examples of typical modifiers are those which are able to influence the acid-base properties of these hydrogenation catalysts, such as, for example, alkali metals and alkaline earth metals and their compounds, especially Mg compounds and Ca compounds, and also phosphoric acid or sulfuric acid and the compounds thereof.

The hydrogenation catalysts can be used in process step b) of the process of the invention in the form of powders or shaped bodies, such as beads, extrudates, rings or compressed powders, for example. Solid catalysts, catalysts of the Raney type or supported catalysts can be employed in the process of the invention. Preference is given to catalysts of the Raney type and supported catalysts. Suitable support materials for these hydrogenation catalysts are, for example, kieselguhr, silicon dioxide, aluminum oxide, aluminosilicates, titanium dioxide, zirconium dioxide, aluminum-silicon mixed oxides, magnesium oxide, and activated carbon. The active metal may be applied to the support material in a way which is known to the skilled person, as for example by impregnation, spraying or precipitation. Depending on the mode of catalyst preparation, further preparatory steps known to the skilled person are required, such as drying, calcining, shaping, and activating, for example. For the purpose of shaping it is possible optionally to add further auxiliaries such as graphite or magnesium stearate, for example.

The hydrogen that is needed for the hydrogenation in process step b) of the process of the invention can be supplied to the reactor either in excess, preferably at up to 10 000 mole equivalents relative to the diimine, or in an amount such as to add not only the hydrogen consumed by the hydrogenation but also that fraction of the hydrogen that leaves the reactor in the product stream. In the case of a continuous regime for the process of the invention, the hydrogen in process step b) may be supplied in cocurrent or countercurrent.

The hydrogenation of the diimine in process step b) of the process of the invention takes place preferably in liquid ammonia as solvent. Per mole of hexodiulose it is preferred to use from 1 to 500 mol, more preferably from 5 to 200 mol, of ammonia. It is useful to use at least that amount of ammonia which was used in the imination in process step a). The fraction of ammonia may also be raised or lowered to the desired level prior to the hydrogenation—process step b)—by addition or removal of ammonia, respectively.

This hydrogenation is preferably carried out without addition of further solvents. It is possible, however, to carry out process step b) as well in the presence of solvent, selected from monohydric alcohols having 1 to 4 carbon atoms, more particularly methanol, and ethers, more particularly tetrahydrofuran, methyl tert-butyl ether or dioxane. The use of mixtures of the abovementioned solvents is possible as well.

The hydrogenation in process step b) of the process of the invention is carried out preferably at a temperature of 20 to 150° C. and more preferably of 40 to 130° C.

A pressure preferably of 0.3 to 50 MPa and more preferably of 2 to 35 MPa is used for the hydrogenation in process step b) of the process of the invention.

The reaction mixture of process step b) in the process of the invention may be worked up in accordance with methods known from the prior art. In particular, in such workup, the ammonia and any solvents possibly used are separated off, and the diamine is isolated.

The hydrocyanation that is likewise possible may generally take place in any way which is known to the skilled person.

Even without further remarks, it is assumed that a skilled person will be able to utilize the above description in its widest scope. The preferred embodiments and examples, consequently, are to be interpreted merely as a descriptive disclosure which in no way has any limiting effect at all.

The present invention is elucidated in more detail below with reference to examples. Alternative embodiments of the present invention are obtainable analogously.

EXAMPLES

1. Oxidation of isosorbitol with AA-Tempo/$O_2$/nitrite/nitrate

Materials:

| | | |
|---|---|---|
| Isosorbitol | 0.1 mol | → 73.62 g/l |
| (1,4: 3,6-dianhydro-D-sorbitol) | | |
| AA-TEMPO | 5 mol % | → 5.365 g/l |
| $NaNO_2$ | 2 mol % | → 2.568 g/l |
| $Mg(NO_3)_2 \times 6H_2O$ | 2 mol % | → 0.712 g/l |
| Acetic acid (100%) | 200 ml | |
| Decane | 7 g | → 35 g/l |
| (internal standard for analysis) | | |

Reaction Conditions:
  Reaction temperature: T=50° C.
  Reaction time: t=4 h
  Oxygen: 10 bar
  Reactor volume: 450 ml
Procedure:
  The starting material, the catalyst, the salts and the internal standard are introduced and are dissolved in the acetic acid (acetic acid is added until the volume of 200 ml is reached) and the solution is transferred to the high-pressure reactor. The reactor is closed and inertized twice with nitrogen. The solution is subsequently heated to a temperature of 50° C. with stirring. At the start of the reaction, 10 bar of oxygen are injected into the autoclave. The pressure in the reactor is held constant at 10 bar, with oxygen consumed being supplemented up to a pressure of 10 bar through an opened oxygen supply line. After four hours, the reaction is discontinued by inertization with nitrogen and cooling of the system.
Result:
  A conversion of more than 97% is observed, with a selectivity for the diketone of 100%.

2. Oxidation of isosorbitol with AA-Tempo/$O_2$/nitrite

Materials:

| | | |
|---|---|---|
| Isosorbitol | 0.1 mol | → 73.10 g/l |
| (1,4: 3,6-dianhydro-D-sorbitol) | | |
| AA-TEMPO | 5 mol % | → 5.335 g/l |
| $NaNO_2$ | 2.5 mol % | → 3.45 g/l |
| Acetic acid (100%) | 200 ml | |

Reaction Conditions:
  Reaction temperature: T=50° C.
  Reaction time: t=4 h
  Oxygen: 10 bar
  Reactor volume: 450 ml Procedure:

The starting material, the catalyst, the salts and the internal standard are introduced and are dissolved in the acetic acid (acetic acid is added until the volume of 200 ml is reached) and the solution is transferred to the high-pressure reactor. The reactor is closed and inertized twice with nitrogen. The solution is subsequently heated to a temperature of 50° C. with stirring. At the start of the reaction, 10 bar of oxygen are injected into the autoclave. The pressure in the reactor is held constant at 10 bar, with oxygen consumed being supplemented up to a pressure of 10 bar through an opened oxygen supply line. After four hours, the reaction is discontinued by inertization with nitrogen and cooling of the system.

Result:

A conversion of more than 97% is observed, with a selectivity for the diketone of 100%.

3. Oxidation of isosorbitol with AA-Tempo/$O_2$/nitrate

Materials:

| | | |
|---|---|---|
| Isosorbitol (1,4: 3,6-dianhydro-D-sorbitol) | 0.1 mol | → 73.23 g/l |
| AA-TEMPO | 5 mol % | → 5.450 g/l |
| $Mg(NO_3)_2 \times 6H_2O$ | 9.3 mol % | → 3.460 g/l |
| Acetic acid (100%) | 200 ml | |
| Decane (internal standard for analysis) | 7 g | → 35 g/l |

Reaction Conditions:
  Reaction temperature: T=50° C.
  Reaction time: t=4 h
  Oxygen: 10 bar
  Reactor volume: 450 ml Procedure:

The starting material, the catalyst, the salts and the internal standard are introduced and are dissolved in the acetic acid (acetic acid is added until the volume of 200 ml is reached) and the solution is transferred to the high-pressure reactor. The reactor is closed and inertized twice with nitrogen. The solution is subsequently heated to a temperature of 50° C. with stirring. At the start of the reaction, 10 bar of oxygen are injected into the autoclave. The pressure in the reactor is held constant at 10 bar, with oxygen consumed being supplemented up to a pressure of 10 bar through an opened oxygen supply line. After four hours, the reaction is discontinued by inertization with nitrogen and cooling of the system.

Result:

A conversion of more than 97% is observed, with a selectivity for the diketone of 100%.

4. Oxidation of isosorbitol with AA-Tempo/$O_2$/nitrite/nitrate

Catalyst amount 50%; salt amount 10% each

Materials:

| | | |
|---|---|---|
| Isosorbitol (1,4: 3,6-dianhydro-D-sorbitol) | 0.1 mol | → 73.25 g/l |
| AA-TEMPO | 2.5 mol % | → 2.70 g/l |
| $NaNO_2$ | 0.2 mol % | → 0.255 g/l |
| $Mg(NO_3)_2 \times 6H_2O$ | 0.2 mol % | → 0.085 g/l |
| Acetic acid (100%) | 200 ml | |
| Decane (internal standard for analysis) | 7 g | → 35 g/l |

Reaction Conditions:
  Reaction temperature: T=50° C.
  Reaction time: t=4 h
  Oxygen: 10 bar
  Reactor volume: 450 ml Procedure:

The starting material, the catalyst, the salts and the internal standard are introduced and are dissolved in the acetic acid (acetic acid is added until the volume of 200 ml is reached) and the solution is transferred to the high-pressure reactor. The reactor is closed and inertized twice with nitrogen. The solution is subsequently heated to a temperature of 50° C. with stirring. At the start of the reaction, 10 bar of oxygen are injected into the autoclave. The pressure in the reactor is held constant at 10 bar, with oxygen consumed being supplemented up to a pressure of 10 bar through an opened oxygen supply line. After four hours, the reaction is discontinued by inertization with nitrogen and cooling of the system.

Result:

A conversion of approximately 47% is observed, with a selectivity for the diketone of 76%.

TABLE 1

Summary of the experiments in the high-pressure reactor on the oxidation of isosorbitol with AA-TEMPO. Reaction temperature 50° C., reaction time 4 h, oxygen 10 bar (line open)

| Example | Isosorbitol [g/l] | AA-TEMPO [g/l] | $NaNO_2$ [g/l] | $Mg(NO_3)_2 \times 6H_2O$ [g/l] | Conversion [%] | Selectivity (diketone) [%] |
|---|---|---|---|---|---|---|
| 1 | 73.62 | 5.365 | 2.568 | 0.712 | 98.4 | 100 |
| 2 | 73.10 | 5.335 | 3.45 | — | 97.8 | 100 |
| 3 | 73.23 | 5.450 | — | 3.460 | 97.9 | 100 |
| 4 | 73.25 | 2.70 | 0.255 | 0.085 | 46.7 | 76 |

5. Oxidation of isosorbitol with AA-Tempo/$O_2$/nitrite/nitrate

Materials:

| | | |
|---|---|---|
| Isosorbitol (1,4: 3,6-dianhydro-D-sorbitol) | 25 mmol | → 73.07 g/l |
| AA-TEMPO | 5 mol % | → 5.35 g/l |
| $NaNO_2$ | 2 mol % | → 2.55 g/l |
| $Mg(NO_3)_2 \times 6H_2O$ | 2 mol % | → 0.70 g/l |
| Acetic acid (100%) | 50 ml | |
| Decane (internal standard for analysis) | 175 g | → 35 g/l |

Figure 1:
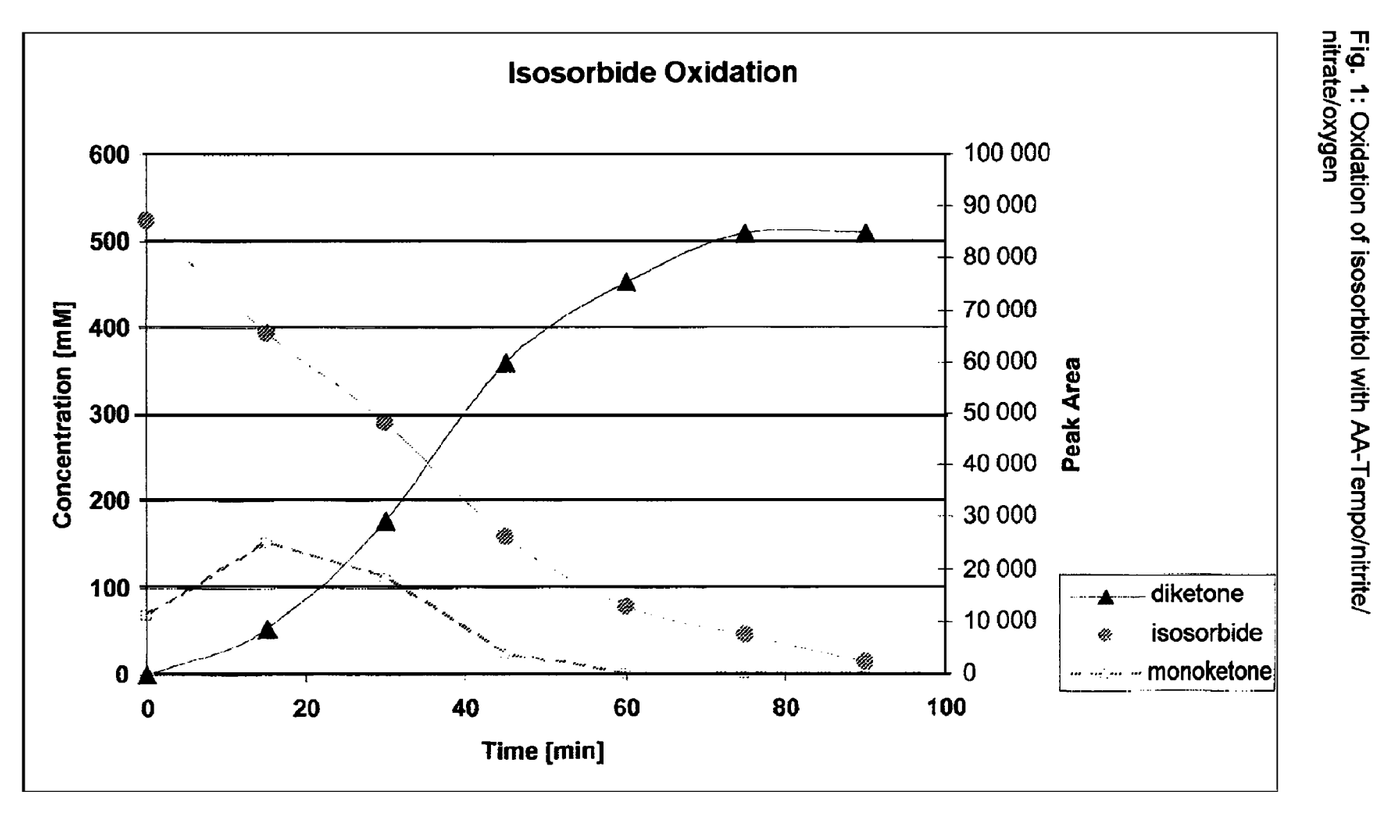
FIG. 1 shows the development in the concentrations of isosorbitol, diketone, and monoketone as a function of time in Example 5.

Reaction Conditions:
 Reaction temperature: T=50° C.
 Reaction time: t=1.5 h
 Oxygen: 10 ml/min
Procedure:
 The starting material, the catalyst, the salts and the internal standard are introduced and are dissolved in the acetic acid (acetic acid is added until the volume of 50 ml is reached) and the solution is transferred to a four-neck flask with reflux condenser, thermometer, gas inlet frit, and septum for sampling. The solution is subsequently heated to a temperature of 50° C. with stirring. At the start of the reaction, oxygen is introduced into the reaction solution via the gas inlet frit with a flow rate of 10 ml/min. The reaction is run over a period of 1.5 hours, with sampling at 15-minute intervals for the purpose of recording the kinetics.
Result:
 A conversion of approximately 97% is observed, with a selectivity for the diketone of 100%.
 FIG. 1 shows the development in the concentrations of isosorbitol, diketone, and monoketone as a function of time when the process of the invention is carried out. The concentrations of isosorbitol and of diketone were evaluated via calibration curves and the internal standard. The monoketone concentrations were evaluated via the peak areas.

6. Oxidation of isosorbitol with AA-Tempo/O$_2$/nitrate

Materials:

| | | |
|---|---|---|
| Isosorbitol (1,4: 3,6-dianhydro-D-sorbitol) | 25 mmol | → 73.07 g/l |
| AA-TEMPO | 5 mol % | → 5.35 g/l |
| Mg(NO$_3$)$_2$ × 6H$_2$O | 4 mol % | → 1.40 g/l |
| Acetic acid (100%) | 50 ml | |
| Decane (internal standard for analysis) | 1.75 g | → 35 g/l |

Figure 2:
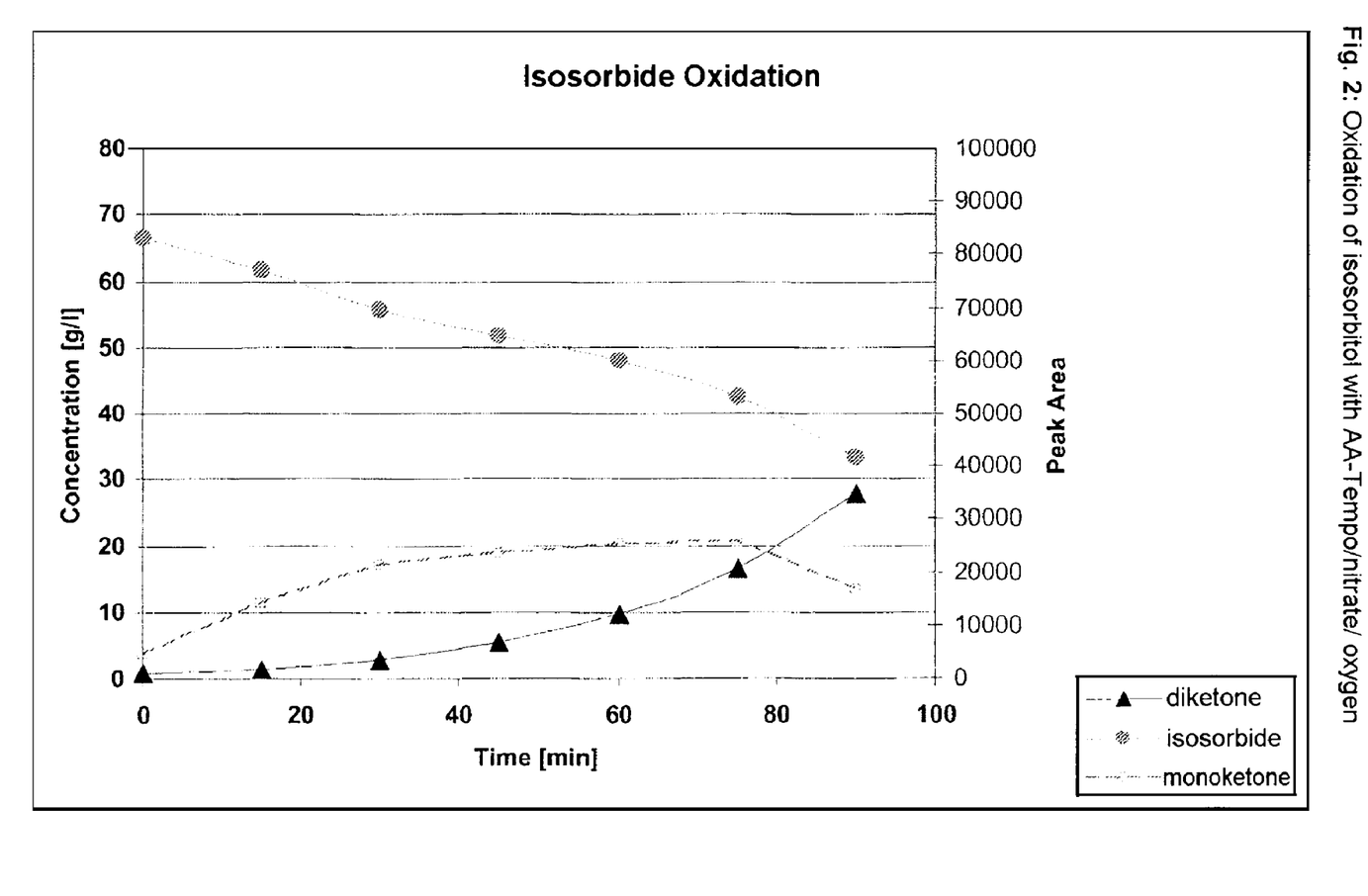
FIG. 2 shows the development in the concentrations of isosorbitol, diketone, and monoketone as a function of time in Example 6.

Reaction Conditions:
 Reaction temperature: T=50° C.
 Reaction time: t=1.5 h
 Oxygen: 10 ml/min
Procedure:
 The starting material, the catalyst, the salts and the internal standard are introduced and are dissolved in the acetic acid (acetic acid is added until the volume of 50 ml is reached) and the solution is transferred to a four-neck flask with reflux condenser, thermometer, gas inlet frit, and septum for sampling. The solution is subsequently heated to a temperature of 50° C. with stirring. At the start of the reaction, oxygen is introduced into the reaction solution via the gas inlet frit with a flow rate of 10 ml/min. The reaction is run over a period of 1.5 hours, with sampling at 15-minute intervals for the purpose of recording the kinetics.
Result:
 A conversion of approximately 36% is observed, with a selectivity for the diketone of approximately 85%.
 FIG. 2 shows the development in the concentrations of isosorbitol, diketone, and monoketone as a function of time when the process of the invention is carried out. The concentrations of isosorbitol and of diketone were evaluated via calibration curves and the internal standard. The monoketone concentrations were evaluated via the peak areas.

7. Oxidation of isomannitol with AA-Tempo/O$_2$/nitrite/nitrate

Materials:

| | | |
|---|---|---|
| Isomannitol (1,4: 3,6-dianhydro-D-mannitol) | 25 mmol | → 73.07 g/l |
| AA-TEMPO | 5 mol % | → 5.35 g/l |
| NaNO$_2$ | 2 mol % | → 2.55 g/l |
| Mg(NO$_3$)$_2$ × 6H$_2$O | 2 mol % | → 0.70 g/l |
| Acetic acid (100%) | 50 ml | |
| Decane (internal standard for analysis) | 175 g | → 35 g/l |

Figure 3:
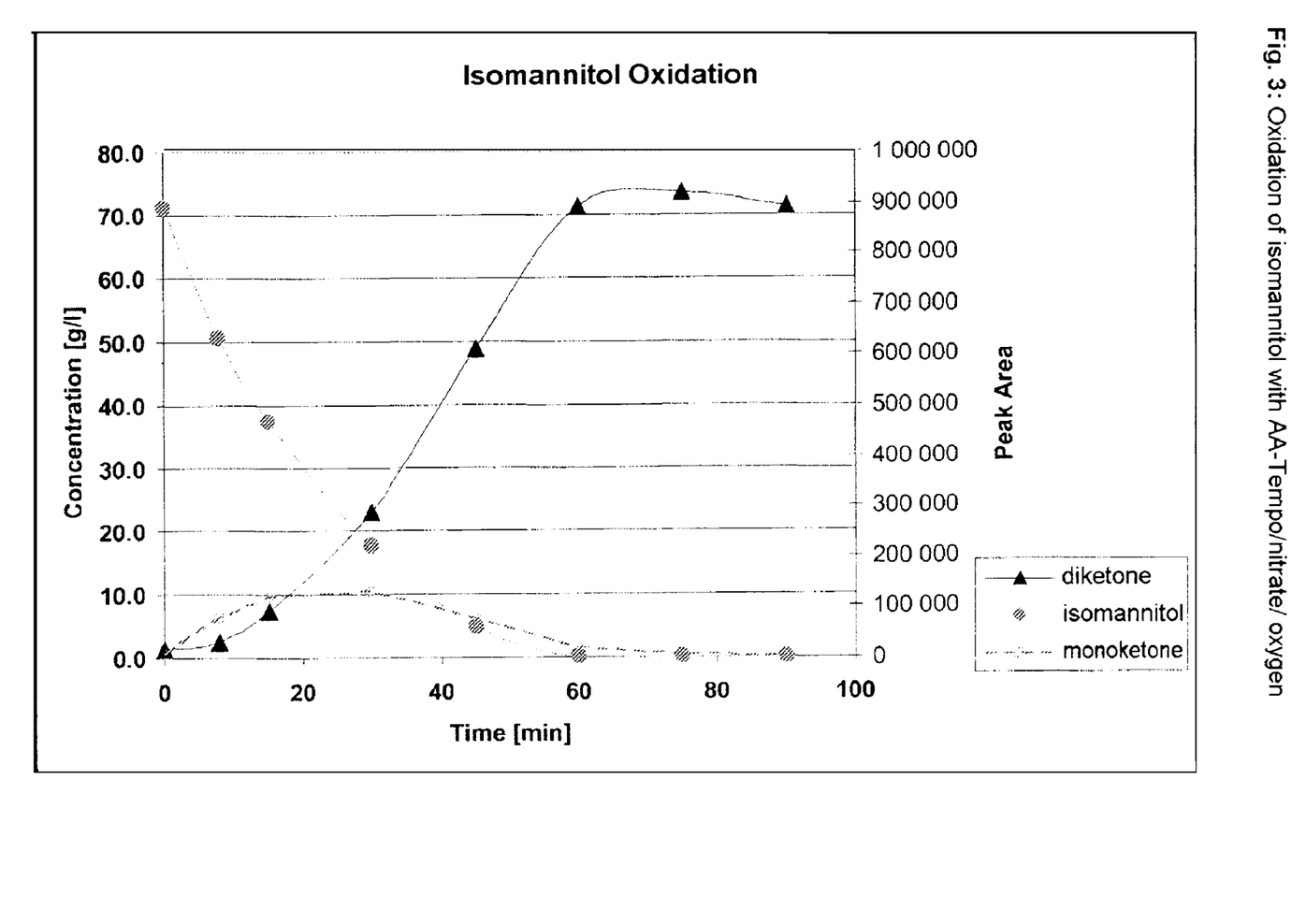
FIG. 3 shows the development in the concentrations of isomannitol, diketone, and monoketone as a function of time in Example 7.

Reaction Conditions:
 Reaction temperature: T=50° C.
 Reaction time: t=1.5 h
 Oxygen: 10 ml/min
Procedure:
 The starting material, the catalyst, the salts and the internal standard are introduced and are dissolved in the acetic acid (acetic acid is added until the volume of 50 ml is reached) and the solution is transferred to a four-neck flask with reflux condenser, thermometer, gas inlet frit, and septum for sampling. The solution is subsequently heated to a temperature of 50° C. with stirring. At the start of the reaction, oxygen is introduced into the reaction solution via the gas inlet frit with a flow rate of 10 ml/min. The reaction is run over a period of 1.5 hours, with sampling at 15-minute intervals for the purpose of recording the kinetics.
Result:
 A conversion of 100% is observed, with a selectivity for the diketone of 100%.
 FIG. 3 shows the development in the concentrations of isomannitol, diketone, and monoketone as a function of time when the process of the invention is carried out. The concentrations of isomannitol and of diketone were evaluated via calibration curves and the internal standard. The monoketone concentrations were evaluated via the peak areas.

TABLE 2

Compilation of the experiments on the oxidation of isosorbitol/isomannitol with AA-Tempo. Reaction temperature 50° C. reaction time 1.5 h, oxygen 10 ml/min

| Example | Isosorbitol [g/l] | AA-TEMPO [g/l] | NaNO$_2$ [g/l] | Mg(NO$_3$)$_2$ × 6H$_2$O [g/l] | Conversion [%] | Selectivity (diketone) [%] |
|---|---|---|---|---|---|---|
| 5 | 73.03 | 5.370 | 2.566 | 0.700 | >97.0 | 100 |
| 6 | 73.53 | 5.384 | — | 1.464 | 36.0 | 84 |
| 7 | isomannitol 73.04 | 5.36 | 2.590 | 0.738 | >99.0 | 100 |

8. Oxidation of isosorbitol with various N-oxy radicals/O$_2$/nitrite/nitrate Materials:

| | | |
|---|---|---|
| Isosorbitol (1,4: 3,6-dianhydro-D-sorbitol) | 10 mmol | → 73.07 g/l |
| N-oxy radical | 5 mol % | |
| NaNO$_2$ | 2 mol % | → 2.55 g/l |
| Mg(NO$_3$)$_2$ × 6H$_2$O | 2 mol % | → 0.70 g/l |
| Acetic acid (100%) | 20 ml | |
| Hexadecane (internal standard for analysis) | 0.05 g | → 2.5 g/l |

Reaction Conditions:
  Reaction temperature: T=50° C.
  Reaction time: t=1.5 h–4.5 h
  Oxygen: 10 ml/min
Procedure:

The starting material, the catalyst and the salts are introduced in a three-neck flask with reflux condenser and gas inlet frit, 20 ml of acetic acid are added, and the mixture is dissolved with stirring. The solution is subsequently heated to a temperature of 50° C. with stirring. At the start of the reaction, oxygen is passed into the reaction solution via the gas inlet frit at a flow rate of 20 ml/min. The reactions are run over a time of 1.5 hours-4.5 hours, with sampling at 30-minute intervals for the purpose of recording the kinetics.

Result:

In accordance with the protocol described above, various N-oxy radicals were used for the reaction. Depending on the N-oxy radical used, the reaction was carried out over a period of 1.5 hours-4.5 hours.

Figure 4:
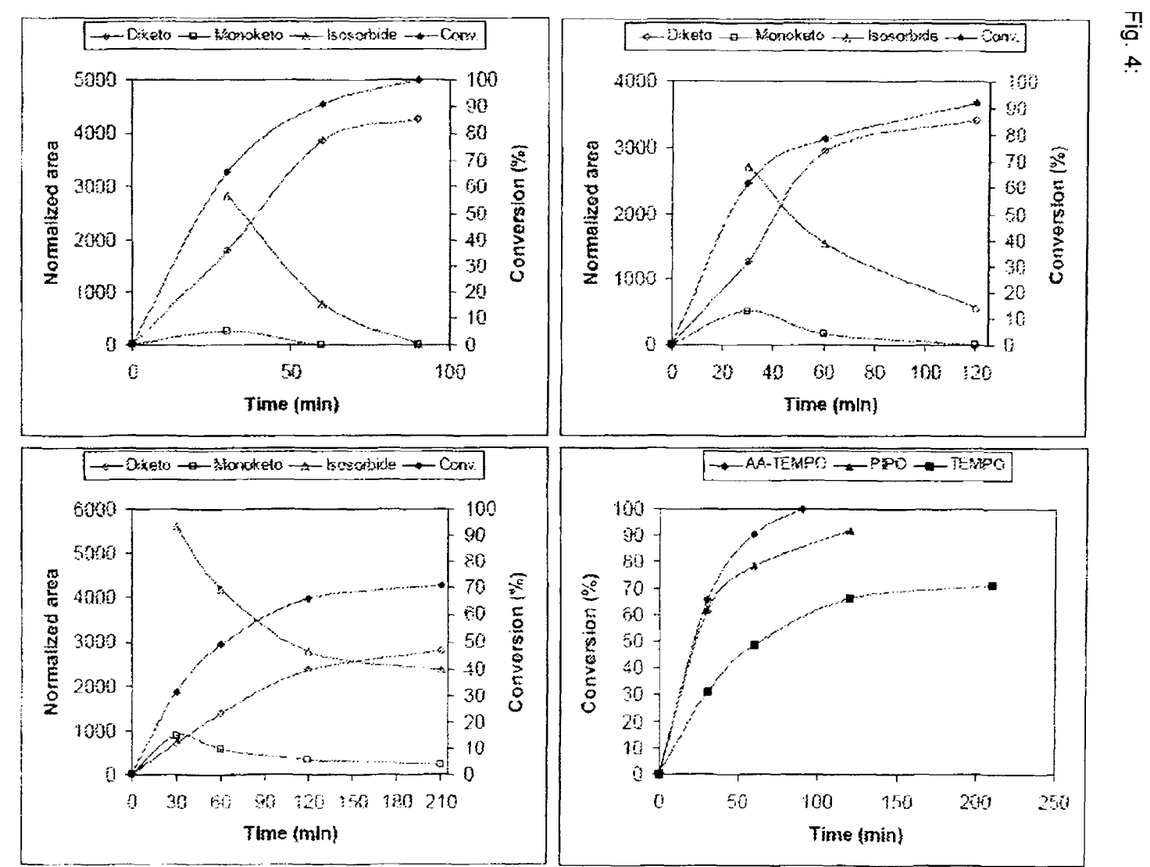
FIG. 4 shows oxidation of isosorbitol with AA-TEMPO (top left), with PIPO (top right), with TEMPO (bottom left), and a comparison of the conversions of all three N-oxy radicals in Example 8.

With AA-Tempo as the N-oxy radical, a conversion of 100% and a selectivity for the diketone of 100% were achieved. FIG. 4 shows the results of the comparative experiments in terms of conversions. The oxidation of isosorbitol with AA-Tempo is shown (top left), with PIPO (top right), with Tempo (bottom left), and a comparison of the conversions of all three N-oxy radicals, as a function of time, is also shown. The graphs show the normalized areas in the GC analysis and the conversion of the isosorbitol in %, evaluated using hexadecane as internal standard.

9. Oxidation of isosorbitol with Tempo/NaClO/bromide (Comparative Example: Hypochlorite Method)

Materials:

| | |
|---|---|
| Isosorbitol (1,4: 3,6-dianhydro-D-sorbitol) | → 20 g/l |
| Tempo | → 1.71 g/l |
| NaBr | → 11.30 g/l |
| NaOCl | → 81.5 g/l |
| Water | → 100 ml |

Reaction Conditions:
  Reaction temperature: T=2-5° C.
  Reaction time: t=2 h
Procedure:

2 g of isosorbitol, 1127 mg of sodium bromide and 171 mg of TEMPO are suspended in 100 ml of water and cooled to 0° C. in an ice-water bath. The continuously measured pH of this mixture is set to a pH of exactly by addition of 0.5 N aqueous sodium hydroxide solution.

The experiment is carried out at a constant pH of 10. This pH is achieved by continuous titration of the resultant acids with 0.5 N aqueous sodium hydroxide solution, the pH value being held constant using TITRINO automatic titration system from Metrohm, Herisau (CH).

Result:

The reaction gives small amounts of monoketone; the desired diketone cannot be found.

The invention claimed is:

1. A process for preparing 2,6-dioxabicyclo[3.3.0]-octane-4,8-dione (I) comprising oxidizing a dianhydrohexitol or corresponding hydroxy-ketone with an oxygen-containing gas in the presence of a catalyst composition comprising at least one nitroxyl radical, one or more NO sources and at least one or more carboxylic acids or their anhydrides and/or mineral acids or their anhydrides, optionally in the presence of one or more solvents, wherein the reaction takes place without addition of halogen sources.

2. The process according to claim 1, wherein nitroxyl radicals are present and are 2,2,6,6-tetramethylpiperidine-1-oxyl (TEMPO) and/or the derivatives of 2,2,6,6-tetramethylpiperidine-1-oxyl which are substituted in position 4 of the heterocycle, the derivatives having one or more substituents selected from the group consisting of $R^1$, $C_1$-$C_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups, where $R^1$ is a $(C_1$-$C_{10})$-alkyl, $(C_1$-$C_{10})$-alkenyl, $(C_1$-$C_{10})$-alkoxy, $(C_6$-$C_{18})$-aryl, $(C_7$-$C_{19})$-aralkyl, $(C_6$-$C_{18})$-aryl-$(C_1$-$C_8)$-alkyl and $(C_3$-$C_{18})$-heteroaryl group.

3. The process according to claim 1, wherein the fraction of nitroxyl radical is 0.001 to 20 mol %, based on the amount of dianhydrohexitol.

4. The process according to claim 1, wherein at least one NO source is present and is nitric acid, nitrous acid, ammonium nitrate or ammonium nitrite, alkali metal or alkaline earth metal nitrates or nitrites, nitrogen oxide-containing gases or mixtures thereof.

5. The process according to claim 1, wherein the fraction of the NO source is 0.001 to 10 mol %, based on the amount of dianhydrohexitol.

6. The process according to claim 1, wherein a carboxylic acid is present and is acetic acid, or an anhydride is present and is acetic anhydride.

7. The process according to claim 1, wherein the fraction of carboxylic acid and/or of anhydride is 0.1 to 200 mol %, based on the amount of dianhydrohexitol present.

8. The process according to claim 1, wherein at least one mineral acid is present and is $H_2CO_3$, $H_3PO_4$, $HNO_3$, $HNO_2$, $H_2SO_4$, $H_2SO_3$, $H_3BO_3$, or their anhydrides or mixtures thereof.

9. The process according to claim 1, wherein no additional solvent is present.

10. The process according to claim 1, wherein the water of reaction is removed from the reaction mixture.

11. The process according to claim 10, wherein the water of reaction is removed by addition of water-absorbing agents to the reaction mixture and/or by distillative or extractive removal from the reaction mixture during the reaction.

12. The process according to claim 10, wherein the solvent is a water-complexing solvent or a solvent which binds water chemically.

13. The process according to claim 1, further comprising removing the carboxylic acid and optionally the solvent by distillation or extraction, extracting and optionally recycling the nitroxyl radicals, optionally removing the salts originating from the NO sources and/or purifying the 2,6-dioxabicyclo[3.3.0]octane-4,8-dione (I) is by crystallization, distillation, extraction and/or chromatographic separation.

14. The process according to claim 1, wherein the 2,6-dioxabicyclo[3.3.0]octane-4,8-dione (I) is subsequently subjected to reductive amination or hydrocyanation.

15. The process according to claim 14, wherein the reductive amination takes place in two stages, a) the 2,6-dioxabicyclo[3.3.0]octane-4,8-dione (I) being converted to the corresponding diimine in the presence of ammonia and b) being subsequently hydrogenated.

* * * * *